US00PP14547P29

(12) United States Plant Patent
Bradford

(10) Patent No.: US PP14,547 P2
(45) Date of Patent: Feb. 17, 2004

(54) NECTARINE TREE NAMED 'BRIGHT SWEET'

(50) Latin Name: *Prunus persica*
Varietal Denomination: Bright Sweet

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 95 days.

(21) Appl. No.: 10/302,973

(22) Filed: Nov. 25, 2002

(51) Int. Cl.[7] ..... A01H 5/00
(52) U.S. Cl. ..... Plt./190
(58) Field of Search ..... Plt./190

(56) References Cited
U.S. PATENT DOCUMENTS

PP9,961 P 7/1997 Bradford

*Primary Examiner*—Anne Marie Grunberg

(57) ABSTRACT

The present invention relates to a nectarine tree, *Prunus persica*, and more particularly to a new and distinct variety broadly characterized by a medium size, vigorous, hardy, self-fertile, productive and regular bearing tree. The fruit matures under the ecological conditions described in late July, with first picking on Jul. 20, 2002. The fruit is uniformly large in size, sub-acidic and very sweet in flavor, globose in shape, clingstone in type, firm in texture, yellow in flesh color, and mostly red in skin color. The variety was developed from an open pollinated seed from an unnamed yellow flesh sub-acid nectarine.

1 Drawing Sheet

Botanical classification: *Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Bright Sweet'. During the spring and summer of 1996 I gathered fruit from several different unnamed seedlings in my experimental orchard at Bradford Farms near Le Grand, Calif. in Merced County (San Joaquin Valley). One particular group of nectarines were yellow in flesh color, clingstone in type, and sub-acidic in flavor, and were thus designated as "YNCSA (OP)". The seeds from this fruit were removed, cracked, stratified, germinated, and grown as seedlings on their own root in my greenhouse, and upon reaching dormancy transplanted to a cultivated area of my experimental orchard described above. During the fruit evaluation season of 1999 I selected several nectarines that exhibited desirable qualities. The present variety was selected as a single tree from the group of "YNCSA (OP)" described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to 'Fire Sweet' (U.S. Plant Pat. No. 9,961) nectarine, by producing nectarines that are nearly globose in shape, very firm in texture, yellow in flesh color, mostly red in skin color, and sub-acidic in flavor, but is distinguished therefrom by being larger in size and maturing about eight days earlier.

SUMMARY OF VARIETY

In summary, the present variety is characterized by a medium size, vigorous, hardy, self-fertile, productive and regular bearing tree. The fruit matures under the ecological conditions described in late July, with first picking on Jul. 20, 2002. The fruit is uniformly large in size, sub-acidic and very sweet in flavor, globose in shape, clingstone in type, firm in texture, yellow in flesh color, and mostly red in skin color.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 25, 2002, on the original tree during its sixth growing season. All major color code designations are by reference to the Inter-Society Color Council, National Bureau of Standards. Common color names are also used occasionally.

Tree

Size: Medium, reaching a height of 9' [2.74 m.] and a spread of 7' [2.13 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and open.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Medium, with a maximum diameter of 2½" [64 mm.] after the sixth growing season.

*Texture.*—Somewhat shaggy.

*Bark color.*—Grayish yellowish brown [80. gy.yBr].

*Lenticels.*—Approximate Number Per Square Inch: 14. Color: Light orange yellow [70. l.OY]. Typical Size: ⅛" to ⅜" [3.2–9.5 mm.].

Branches:

*Size.*—Diameter of limb is 1¼" [32 mm.] measured 12" above the crotch, typical of *Prunus persica*, and dependent upon cultural practices and climatic conditions.

*Texture.*—Smooth on 1st year wood, increasing roughness with age.

*Color.*—1st Year Wood Topside: Grayish red [19. gy.R]. 1st Year Wood Underside: Brilliant yellow green [116. brill.YG]. Older Wood: Dark yellowish brown [78. d.yBr].

*Lenticels.*—Approximate Number Per Square Inch: 50. Color: Light yellowish brown [76. l.yBr]. Typical size: 1/32" to ⅛" [0.8–3.2 mm.].

Leaves:

*Size.*—Medium. Average Length: 5¼" [133 mm.]. Average Width: 1½" [38 mm.].

*Arrangement.*—Alternate.

*Thickness.*—Medium.

*Form.*—Elliptical.

*Apex.*—Acuminate.

*Base.*—Acute, with an average base angle of 90 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: 7/16" [11.1 mm.]. Average Thickness: 1/16" [1.6 mm.]. Color: Brilliant yellow green [116. brill.YG].

*Stipules.*—Number: 2 per leaf, up to 4 per growing tip. Average Length: ⅜" [9.5 mm.]. Color: Strong yellow green [117. s.YG] becoming Moderate reddish brown [43. m.rBr] when old and dry.

*Glands.*—Number: 2 to 6. Position: Usually opposite, positioned on both the petiole and base of blade. Size: Small. Form: Appear to be globose when infant, but take on reniform shape with maturity. Color: Brilliant yellow green [116. brill.YG] on younger leaves acquiring Moderate reddish brown [43. m.rBr] centers with age.

*Leaf buds.*—Conic.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepals and petal locations alternately positioned.

*Type.*—Showy, large.

*Average flower diameter.*—1⅝" [41.3 mm.].

*Number of petals.*—Usually five.

*Petal shape.*—Circular to oval.

*Petal margin.*—Somewhat wavy.

*Average petal diameter.*—11/16" [17.5 mm.].

*Average petal length.*—13/16" [20.6 mm.].

*Petal apex.*—Rounded with a small notch located at the top center of the margin on many.

*Petal base.*—Rounded to slightly truncate.

*Petal color.*—Pale purplish pink [252. p.pPk].

*Anther color.*—Dark red [16. d.R] over a Brilliant orange yellow [67. brill.OY] center.

*Stigma color.*—Light greenish yellow [101. l.gY].

*Sepal color.*—Grayish purplish red [262. gy.pR].

*Sepal length.*—¼" [6 mm.].

*Sepal width.*—3/16" [5 mm.].

*Average pistil length.*—¾" [19.1 mm.].

*Average stamen length.*—⅝" [15.9 mm.].

*Fragrance.*—Moderate.

*Blooming period.*—Medium compared with other varieties.

*Onset of bloom.*—One percent on Mar. 2, 2002.

*Date of full bloom.*—Mar. 12, 2002.

*Duration of bloom.*—One to two weeks, dependent on ambient temperature.

*Number per cluster.*—1 to 3 with single flowers most common.

FRUIT

Maturity when described: Firm ripe, Jul. 25, 2002.

Date of first picking: Jul. 20, 2002.

Date of last picking: Jul. 31, 2002.

Size: Uniform, large.

*Average diameter axially.*—3" [76.2 mm.].

*Average diameter across suture plane.*—3" [76.2 mm.].

*Typical weight.*—9.2 ounces [261 grams].

Form: Uniform, globose, symmetrical.

*Longitudinal section form.*—Circular to oval.

*Transverse section through diameter.*—Circular.

Suture: A sharp crack from the stem to the shoulder, a shallow rounded trough along the side, and a deeper groove toward the apex that discontinues with a marked depression just beyond the pistil point.

Ventral surface: Rounded, lipped toward the apex.

Lips: Fairly equal.

Cavity: Flaring, elongated in the suture plane, suture showing on one side, Light yellow [86. l.Y] stem markings typical.

*Depth.*—¾" [19.1 mm.].

*Breadth.*—1⅛" [27.0 mm.].

Base: Truncate.

Apex: Rounded, cuneate when viewed along the suture.

Pistil point: Apical, negligible in length, depressed within the suture.

Stem: Medium.

*Average length.*—⅜" [9.5 mm.].

*Average width.*—3/16" [4.8 mm.].

Skin:

*Thickness.*—Medium.

*Surface.*—Smooth.

*Tenacity.*—Tenacious to flesh.

*Astringency.*—Nonastringent.

*Tendency to crack.*—None observed in dry season.

*Color.*—Very deep red [14. v.deep R] over a Strong red orange [35. s.rO] background with Light orange yellow [70. l.OY] freckling on the sides toward the apex.

Flesh:

*Color.*—Brilliant yellow [83. brill.Y] with Dark red [16. d.R] streaking close to the stone.

*Surface of pit cavity.*—Dark red [16. d.R] fibers breaking when twisted from the stone.

*Amygdalin.*—Scarce.

*Juice.*—Abundant, rich.

*Texture.*—Very firm, crisp.

*Fibers.*—Abundant, fine.

*Ripens.*—Slightly earlier toward the apex.

*Flavor.*—Sub-acid and very sweet, averaging 18 brix.

*Aroma.*—Slight.

*Eating quality.*—Excellent.

STONE

Type: Clingstone.
Form: Oval.
External color: Dark reddish brown [44. d.rBr].
Internal cavity color: Deep brown [56. deep Br].
Hilum: Narrow, oblong.
Base: Straight.
Apex: Acute, with an average tip angle of 90 degrees.
Sides: Equal.
Surface: Irregularly furrowed near the apex and pitted toward the base.
Ridges: Jagged toward the base.
Average pit wall thickness: ¼" [6.4 mm.].
Average width: 1" [25.4 mm.].
Average length: 1 7/16" [36.5 mm.].
Average breadth: ¾" [19.1 mm.].
Tendency to split: Slight.

Kernel:

*Form.*—Oval.

*Skin color.*—Pale orange yellow [73. p.OY] when freshly removed.

*Pellicle color.*—Grayish yellowish brown [80. gy.yBr].

*Vein color.*—Dark orange yellow [72. d.OY].

*Taste.*—Sweet.

*Viable.*—Yes.

*Average width.*—½" [12.7 mm.].

*Average length.*—¾" [19.1 mm.].

*Amygdalin.*—Scant.

USE

Market: Fresh market and long distance shipping.
Keepinq quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Fire Sweet' (U.S. Plant Pat. No. 9,961) nectarine, by producing nectarines that are nearly globose in shape, very firm in texture, yellow in flesh color, mostly red in skin color, and sub-acidic in flavor, but is distinguished therefrom by being larger in size and maturing about eight days earlier.

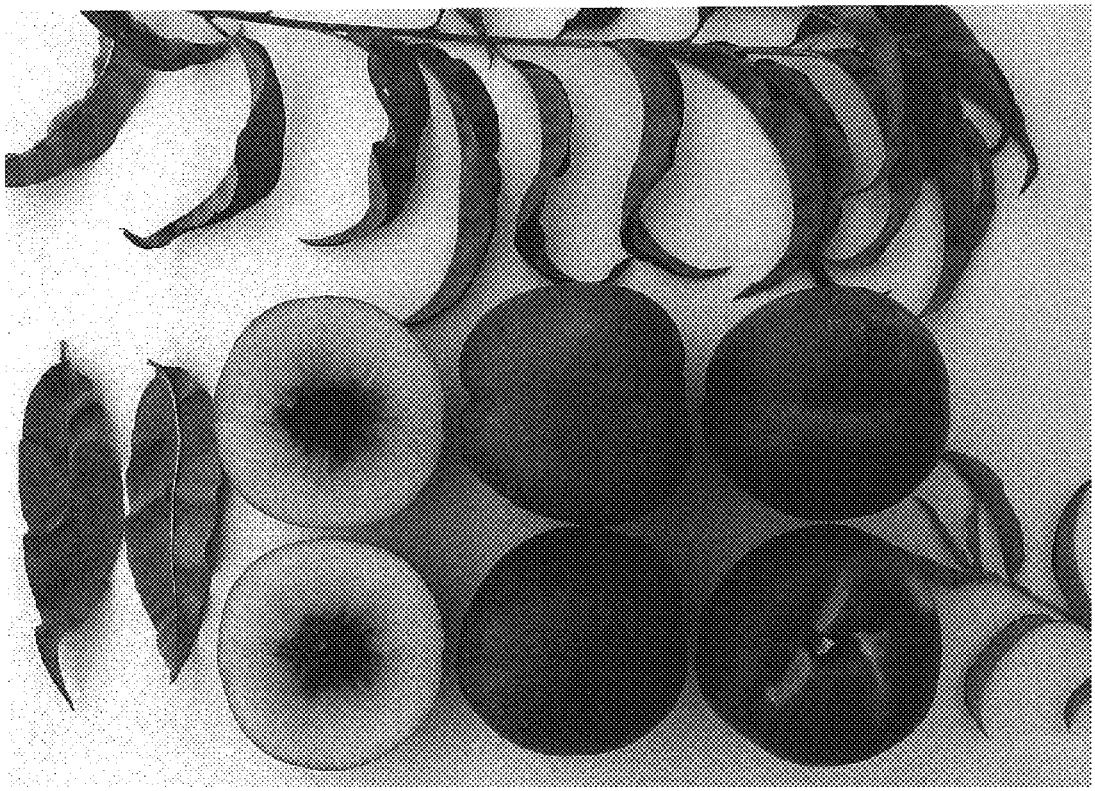

* * * * *